United States Patent
Yu et al.

(10) Patent No.: US 11,639,021 B2
(45) Date of Patent: May 2, 2023

(54) METHOD AND DEVICE FOR PRODUCING VASCULATURE THROUGH EXTRUSION-BASED 3D PRINTING

(71) Applicant: CARNEGIE MELLON UNIVERSITY, Pittsburgh, PA (US)

(72) Inventors: Zhou Yu, Pittsburgh, PA (US); Philip R. LeDuc, Wexford, PA (US); O. Burak Ozdoganlar, Sewickley, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 126 days.

(21) Appl. No.: 16/537,499

(22) Filed: Aug. 9, 2019

(65) Prior Publication Data

US 2020/0047401 A1 Feb. 13, 2020

Related U.S. Application Data

(60) Provisional application No. 62/764,570, filed on Aug. 9, 2018.

(51) Int. Cl.
| | |
|---|---|
| *B29C 64/106* | (2017.01) |
| *B29C 64/20* | (2017.01) |
| *B33Y 10/00* | (2015.01) |
| *B33Y 30/00* | (2015.01) |
| *B33Y 70/00* | (2020.01) |

(Continued)

(52) U.S. Cl.
CPC ............ *B29C 64/106* (2017.08); *A61L 27/20* (2013.01); *A61L 27/222* (2013.01); *A61L 27/26* (2013.01); *B29C 64/20* (2017.08); *B33Y 10/00* (2014.12); *B33Y 30/00* (2014.12); *B33Y 70/00* (2014.12); *B33Y 80/00* (2014.12); *B29K 2067/043* (2013.01); *B29K 2105/0061* (2013.01);

(Continued)

(58) Field of Classification Search
CPC .... A61L 2400/08; A61L 27/20; A61L 27/222; A61L 27/26; A61L 27/56; B01F 13/0023; B01F 15/0279; B01F 7/0005; B01F 7/00408; B29C 64/106; B29C 64/20; B29C 64/209; B29C 64/336; B29C 64/321; B29C 48/362; B29C 48/363; B29C 64/40; B29K 2067/043; B29K 2105/0061; B29K 2105/24; B29K 2995/0056; B29L 2031/7532; B33Y 10/00; B33Y 30/00; B33Y 70/00; B33Y 80/00
See application file for complete search history.

(56) References Cited

U.S. PATENT DOCUMENTS

| | | | |
|---|---|---|---|
| 2018/0272599 A1* | 9/2018 | Rodriguez | ............... C08L 63/00 |
| 2019/0077047 A1* | 3/2019 | Andrews | ............... B29C 48/286 |

OTHER PUBLICATIONS

Glick et al_Microsystems & Nanoengineering (2016) 2, 16063 (Year: 2016).*

(Continued)

*Primary Examiner* — Yunju Kim
(74) *Attorney, Agent, or Firm* — Michael G. Monyok

(57) ABSTRACT

A method and device for fabricating vascular networks in for tissue engineering. The vascular network is embedded in a porous scaffold and is created from a sacrificial wax template, according to one embodiment. A extrusion-based three dimensional printer is used to create the template, wherein the printer utilizes an extruder incorporating a mixer to maintain the consistency of the extrudate.

5 Claims, 5 Drawing Sheets

(51) Int. Cl.
*B33Y 80/00* (2015.01)
*A61L 27/20* (2006.01)
*A61L 27/22* (2006.01)
*A61L 27/26* (2006.01)
*B29K 105/24* (2006.01)
*B29K 105/00* (2006.01)
*B29K 67/00* (2006.01)
*B29L 31/00* (2006.01)

(52) U.S. Cl.
CPC .. *B29K 2105/24* (2013.01); *B29K 2995/0056* (2013.01); *B29L 2031/7532* (2013.01)

(56) References Cited

OTHER PUBLICATIONS

Ma et al_Biomaterials 24 (2003) 4833-4841 (Year: 2003).*
Wan et al_Micromachines 2020 11 907 (Year: 2020).*
Whang et al_Polymer vol. 36 No. 4 837-842, 1995 (Year: 1995).*
Tocchio, A. et al. "Versatile fabrication of vascularizable scaffolds for large tissue engineering in bioreactor." Biomaterials 45 (2015): 124-131.
Sachlos, E. et al. "Novel collagen scaffolds with predefined internal morphology made by solid freeform fabrication." Biomaterials 24, No. 8 (2003): 1487-1497.

\* cited by examiner

METHOD AND DEVICE FOR PRODUCING VASCULATURE THROUGH EXTRUSION-BASED 3D PRINTING

CROSS-REFERENCE TO RELATED APPLICATIONS

This application claims priority and the benefit of the filing date based on U.S. provisional application No. 62/764,570, filed Aug. 9, 2018, under 35 USC § 119, where the provisional application is hereby incorporated by reference.

STATEMENT REGARDING FEDERALLY SPONSORED RESEARCH

Not applicable.

BACKGROUND OF THE INVENTION

The invention relates to a method and device for fabricating biomimetic structures having vasculature. More specifically, this invention relates to a method utilizing an extrusion-based three-dimensional (3D) printer used to create a scaffold containing vasculature that can be used for engineered tissues.

Developing engineered tissues with high fidelity to the native ones is important in a multitude of applications from patient-specific transplantation to lab-on-a-chip devices. A tremendous challenge though has been in creating thick and physiologically-relevant tissues. Many human and animal tissues naturally possess 3D topographies enabling certain physiological functions. Absence of these topographies in engineered tissues may undermine the effectiveness of corresponding tissue repair and regeneration. However, thick tissues require intricate vascular networks to supply sufficient oxygen and nutrients to the embedded cells in tissue matrix and take on carbon dioxide and waste products.

Tissue-engineered topographies and vasculature are two big challenges that have been extensively investigated. However, neither feature has been successfully reconstructed to replicate the physiological functions in nature. Moreover, as these features typically are naturally found at the micro-scale, the strength and stability of the features during long-time culture and extensive remodeling in engineered tissues are factors that must be considered.

Intricate vascular networks maintain the viability of cells throughout thick tissues by supplying oxygen and nutrients to the surrounding cells and removing waste products. In fact, cells cannot survive when located farther than 200 μm from a blood vessel. In systemic circulation, oxygen-rich blood leaves the left ventricle of heart through the aorta (~25 mm in diameter), through a vascular network of vessels having a decreasing diameter, and eventually into thin walled capillaries (<10 μm in diameter). Blood travels slowly as the red blood cells are squeezed through the capillaries, releasing oxygen, nutrients and other important substances while taking on carbon dioxide and waste substances. While directly creating capillaries is possible, certain advantages can be realized when creating them via directed capillary growth (e.g., angiogenesis). Thus, current efforts to engineer vascularized tissues are focused on vessels ranging from 100 μm to 1 mm in diameter, where micro-scale capillaries can be formed subsequently through controlled angiogenesis.

Engineered tissues or organs are often developed using tissue scaffolds, cells, and growth factors. When creating a scaffold, it is critical to meet material and microstructure (porous or fibrous) requirements for fostering cell adhesion and growth as well as transport of nutrients and waste. To this end, biomaterials such as natural (e.g., collagen and gelatin) or synthetic (e.g., polylactic acid and polyglycolic acid) polymers that are biocompatible have been used as scaffold materials. Furthermore, different chemical or physical crosslinkers have been added to the biomaterials to tailor their biodegradability to ensure that the scaffolds retain the required micro-architectures until the cells fully grow into a tissue. To create a microstructure suitable for cell growth, appropriate pore size of the porous scaffold must be considered.

Various scaffold fabrication techniques have been developed and demonstrated, such as solvent casting/particle leaching, solvent casting/gas foaming, direct gas foaming, lyophilization, electrospinning, 3D printing, and hybrid methods combining two or more of those techniques. Most of the techniques can achieve well controlled and reproducible porous structures using various biocompatible polymers. Porous scaffolds usually have favorable mechanical properties and adjustable biodegradability, which can maintain the tissue structures during long-term cultivation and extensive tissue remodeling. However, tissue scaffolds only with porous structure are not intricate enough to reconstruct all the physiological functions after introducing cells. For example, porosity can be too high, requiring a long time for the tissue to remodel. Alternatively, pore size that is too small can limit cell migration. More importantly, these processes do not incorporate vasculature into the scaffold, instead relying on angiogenesis.

To overcome these deficiencies, attempts have been made to create engineered tissues with vascular networks. An efficient engineered vasculature requires controllable vascular geometry, proper vessel density, high patency rate, and clear locations for natural or surgical anastomosis. Diverse technical schemes have been reported to create vascularized tissues, including: (i) self-vascularization (direct introducing endothelial cells in tissue matrix), (ii) geometry-guided vascularization (defining boundaries of lumens in tissue matrix that are subsequently seeded with endothelial cells), and (iii) angiogenesis (stimulating capillary self-generation from existing vessels). However, these approaches have drawbacks, including random organization of the vascular network with no capability of controlling vascular geometries, lack of long-term functionality, meshed vessel walls that inhibit cell attachment, thick walls that inhibit material exchange, or use of scaffold materials that provide only temporary structural support. For example, many processes use biopolymers comprising soft hydrogels which are crosslinked under mild conditions due to loaded cells, thereby creating a fragile structure that does not permit extensive tissue remodeling.

Therefore, it would be advantageous to develop a method and device for producing engineered tissues with vasculature that have sufficient mechanical strength and biological stability to maintain these physiological features under long-term culture and extensive remodeling.

BRIEF SUMMARY

According to embodiments of the present invention is a method of producing tissue scaffolds that incorporate vascular networks. The vascular network is formed using an extrusion-based three dimensional (3D) printer. Once formed, the vascular template is embedded in a hydrogel solution during fabrication of the scaffold. After lyophilization and crosslinking, thereby forming a structurally robust scaffold, the template can be removed by melting the wax. Subsequently, cells can be introduced to the lumens and pores of the scaffold. The 3D printer incorporates a hybrid mixer/extruder to maintain a homogeneous mixture of solid/liquid wax, which is heated to near its melting point during the extrusion-based printing.

DETAILED DESCRIPTION

Figure 1A:
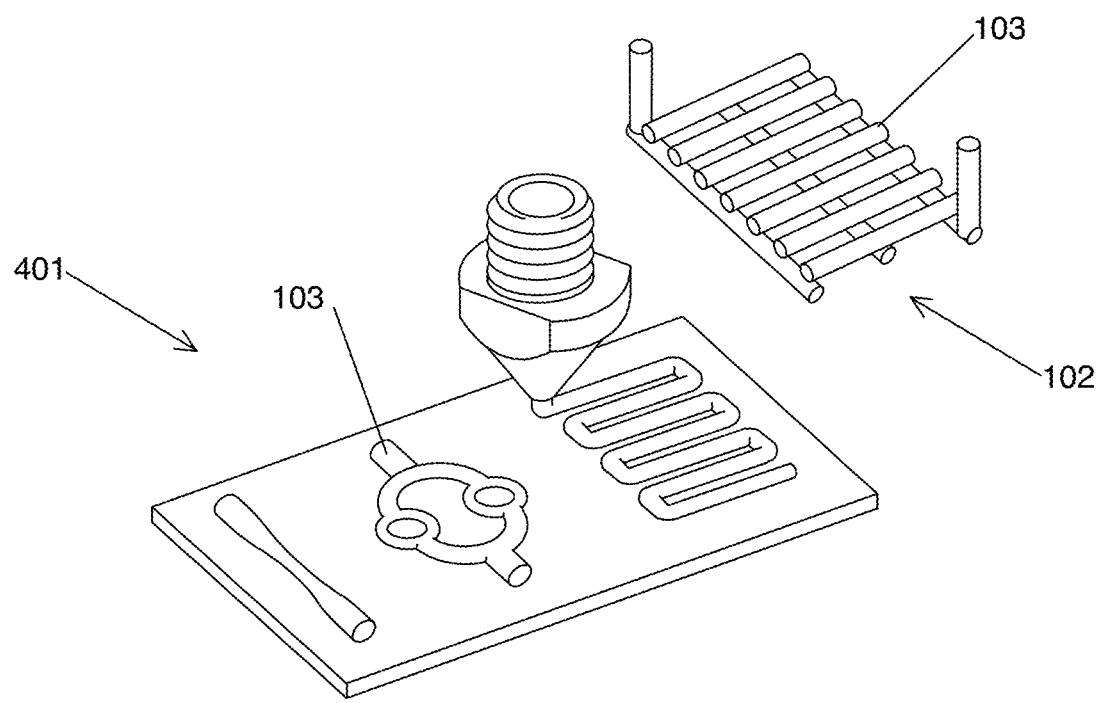
FIGS. 1A-1E depict various step of the method, according to one embodiment.
Figure 1B:
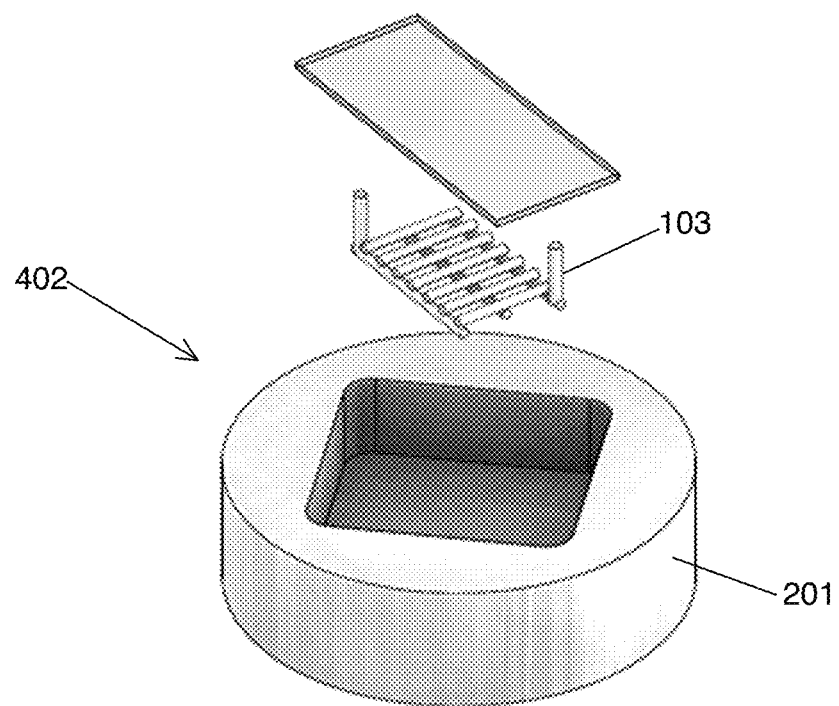
Figure 1C:
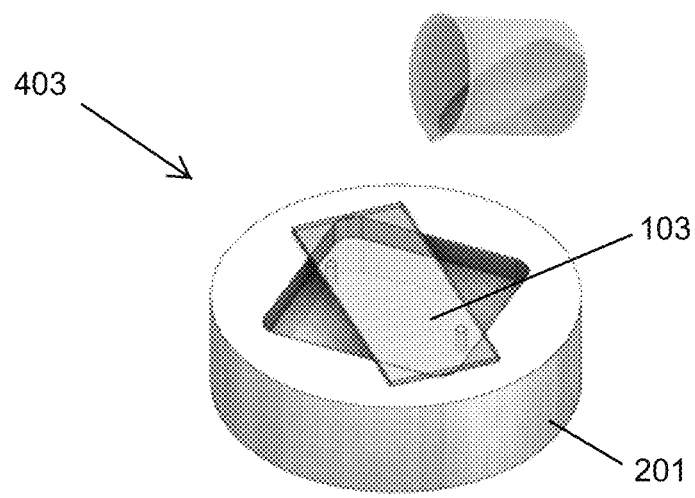
Figure 1D:
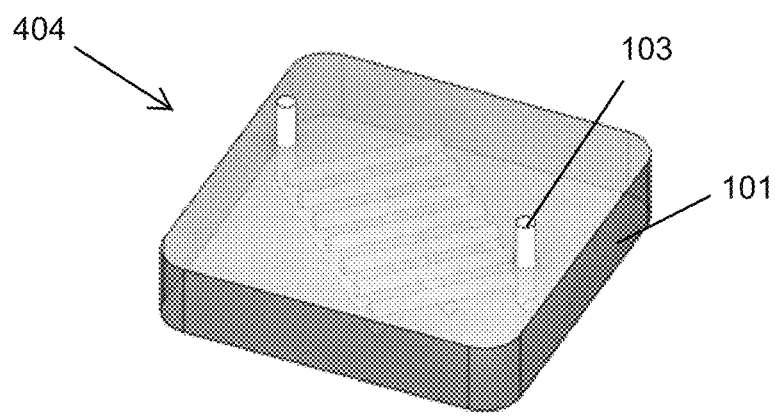
Figure 1E:
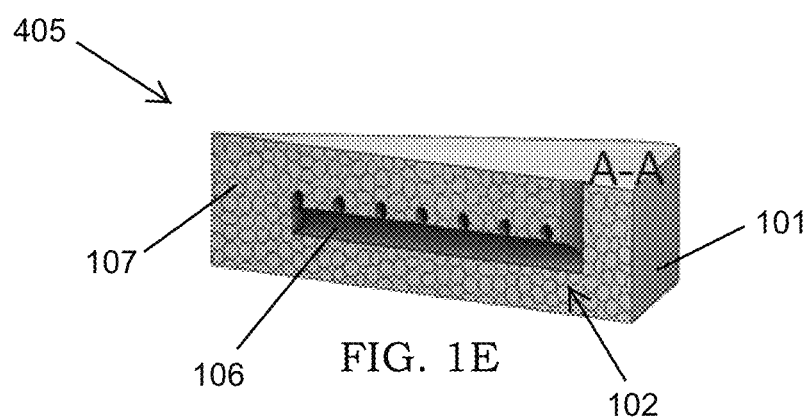

According one embodiment of the present invention is a method of fabricating engineered tissues with a biomimetic material comprising a porous tissue scaffold 101 incorporating a vascular network 102. In one example embodiment, the scaffold 101 comprises a hydrogel, such as Gel-C6S-HA, created through lyophilization. In this example embodiment, Gel-C6S-HA is selected as the material for the scaffold 101 due to its biocompatibility, inherent biodegradability, and other important characterizations, such as facilitation of cell attachment. To create the scaffold 101, gelatin (5 wt % of Gel, cat #G-2500, Sigma-Aldrich), chondroitin-6-sulfate (0.05 wt % of C6S, cat #C-4384, Sigma-Aldrich), and hyaluronic acid (0.2 wt % of HA, cat #H-5388, Sigma-Aldrich) are added to autoclaved deionized water at room temperature. The solution was then mixed using a magnetic hotplate stirrer (SCILOGEX MS-H-ProT) at 35° C. and 500 rpm for 2 hours. The prepared hydrogel solution is poured into a polydimethylsiloxane (PDMS) reservoir 201.

In the freezing stage, the production reservoir 201 loaded with the hydrogel solution is frozen in a freezer (Thermo REVCO) at an approximate freezing rate <1° C. per minute from room temperature to −20° C., and kept at −20° C. for at least 3 hours, such that the water in the hydrogel solution formed ice crystals within desired size range. In the second stage, the hydrogel samples are lyophilized using a freeze-dryer (LABCONCO FREEZONE 4.5) overnight at −40° C. under $90 \times 10^{-3}$ mBar pressure, where the water is sublimated to create porous scaffolds 101. The hydrogel scaffolds 101 are covalently crosslinked using N'-(3-(dimethylamino) propyl)carboiimide/N-hydroxysuccinimide (EDC/NHS) to tailor their biodegradability so that they retained their 3D micro-architecture in a culture medium. In this example, the scaffolds 101 exhibit interconnected (open) pores with pore sizes ranging from 50-300 µm.

To improve long-term functionality when used for tissue engineering, the scaffold 101 can include a vascular network 102. A pre-vascularized porous scaffold 101 improves tissue survival, especially since self-vascularization of cells can take a significant amount of time to reach the vessel maturation. Further, with self-vascularization, it can be hard to control the vascular density and geometries. In contrast, a vascularized porous scaffold 101 provides a void space that potentially facilitates angiogenesis. As it is difficult to fabricate vessels at the size and density of capillaries, it can be beneficial to allow angiogenesis to happen at a later stage, when the engineered larger vessels are mature.

In one embodiment, a sacrificial template 103 is used to introduce the vascular network 102 into the scaffold 101 during fabrication of the scaffold 101. In this example embodiment, the template 103 comprises polyester wax that is created through the use of an extrusion-based 3D printer 300. To introduce the template 103, the hydrogel solution is cast over the template 103, prior to lyophilization. This process creates a porous hydrogel scaffold 101 with an intricate vasculature 102 embedded, where the vascular network 102 includes structures having circular cross-sections, controllable geometries, and an integral barrier between the embedded vasculature and surrounding pores of the scaffold 101.

FIG. 1 depicts the fabrication approach used for the preparation of a porous scaffold 101 with the embedded vascular networks 102. The approach involves five distinct processing steps. At step 401 (FIG. 1A), a sacrificial vascular template 103 with prescribed geometries is manufactured from a thermally reversible material, such as polyester wax. In one embodiment, the template 103 is manufactured using an extrusion-based 3D printer 300. At step 402 (FIG. 1B), the template 103 is suspended in a reservoir 201 by gluing the template 103 to a piece of coverslip and placing the coverslip on the edge of the reservoir 201. Next, at step 403 (FIG. 1C), a hydrogel solution is cast in the reservoir 201 and subsequently frozen with a controlled cooling rate. When small filaments are cast in hydrogel solution, they slowly absorb moisture and slightly deform. To avoid this absorption, a thin layer of poly(D-lactide-co-glycolide) (PDLGA) may be used on the filaments before casting the hydrogel solution. At step 404 (FIG. 1D), lyophilization of the frozen hydrogel produces a porous scaffold 101 with the wax templates 103 embedded within the scaffold 101. Finally, at step 405 (FIG. 1E), the lyophilized scaffolds 101 are crosslinked using a chemical crosslinker to tune their biodegradability. At this stage, the wax template 103 can be removed under light vacuum after warming the whole scaffold to liquefy the template material. Since cells have not been introduced during the fabrication process, chemical crosslinking can be applied to significantly improve the mechanical strength and biostability of the scaffold 101. After crosslinking, cells, such endothelial cells (i.e. HUVECs) and fibroblasts (i.e. NHFs), can be introduced to the lumens 106 and pores 107 of the scaffold 101, respectively.

Figure 2:
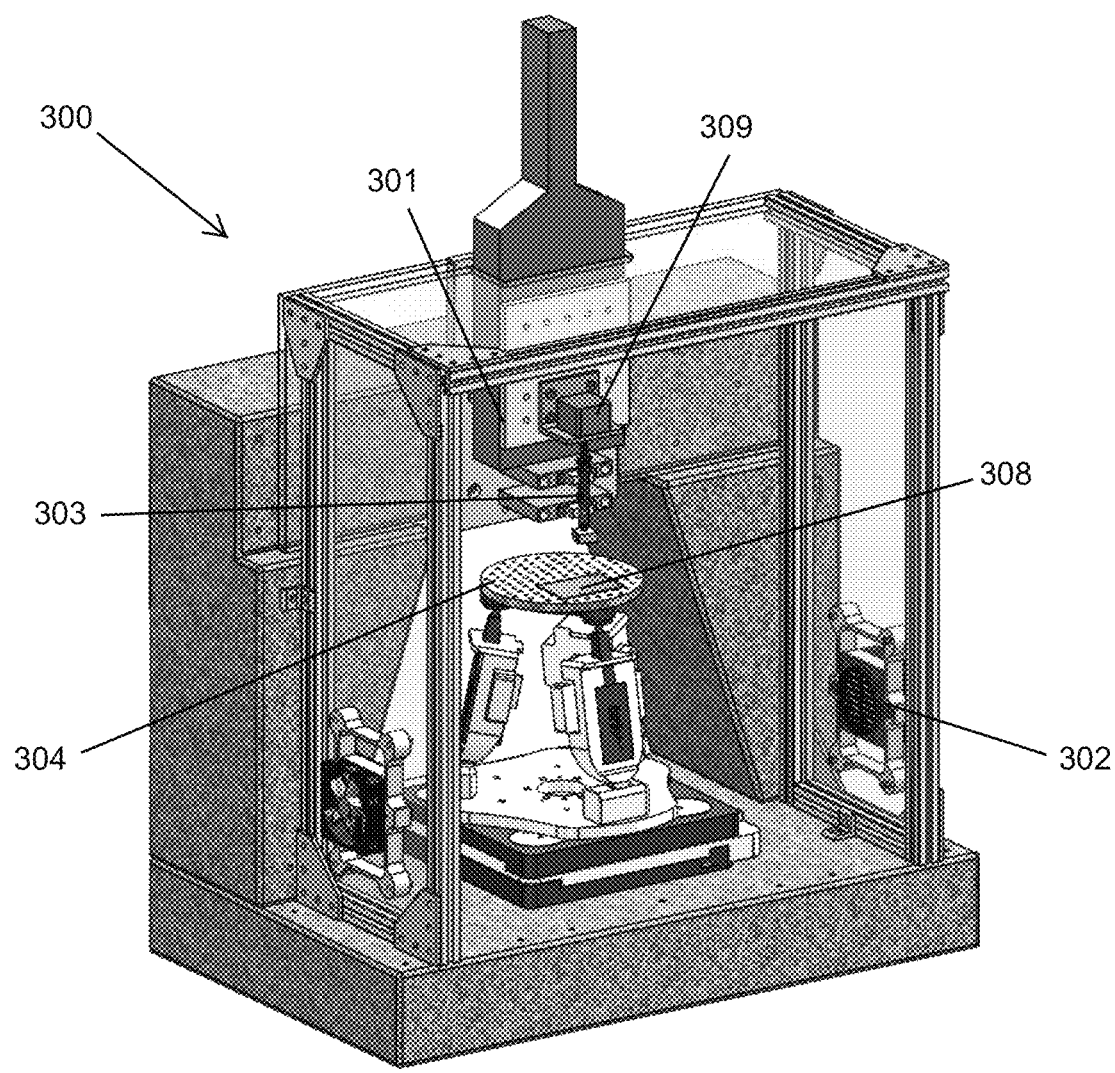
FIG. 2 shows an extrusion-based 3D printer used to create sacrificial vascular templates.

Referring again to step 401, the template 103 is fabricated using an extrusion-based 3D printer 300, as shown in FIG. 2. Using a printer 300, the template 103 can be fabricated to be structurally resilient (i.e. no breakage or deformation when suspended), using a material that resists dissolving in the hydrogel solution or crosslinking chemical, to contain no water to avoid damage during lyophilization, to possess appropriate surface tension and affinity to adsorb enough hydrogel molecules to its surface to form a barrier between the vasculature 102 and pores 107, and to be easily removable from the hydrogel scaffold 101. In one embodiment, a synthetic polyester wax is used for the template 103 because it has a low melting point (37° C.) and is soluble in most organic solvents (e.g. alcohols), but not in water. Further, polyester wax can hold its own structure in the shape of circular fiber as fine as 200 µm in diameter.

One disadvantage of polyester wax is that it does not have a consistent viscoelastic property. It is completely solid at room temperature, while it is a clear liquid with very low viscosity at a temperature above 37° C. When a portion of wax is gradually heated from room temperature to its melting point, part of the wax begins to melt while the other part remains a solid. Stated differently, it is difficult to obtain a homogeneous texture with a favorable viscosity for extrusion when relying on heat alone. As a result, the extrusion-based 3D printer 300 requires mixing of the part-solid/part-liquid wax near its melting point during printing.

In one embodiment, the printer 300 comprises a linear motion stage 301, a heating system 302, an extruder 303 incorporating a mixer 307, and a 5-axis stage 304, as shown in FIG. 2. In this example embodiment, a 5-axis stage (customized, Alio Industries) and a linear motion stage 301 with high load capacity (ATS02005-M-40P, Aerotech) are used for wax extraction and deposition. The 5-axis stage 304 can travel along XYZ axis and rotate along BC axis, with encoder resolution at 5 nm and maximum tripod speed at 200 mm/sec. A substrate 308, such as a glass slide, is placed and fixed on the stage 304 to collect the printed wax. The travel path of the 5-axis stage 304 determines the final geometry of the wax extrudate. The linear motion stage 301 is mounted on a frame of the 5-axis stage. The linear motion stage 301 can travel along Z axis only, with resolution at 1 um, maximum travel speed at 160 mm/s and maximum side load at 25 kg. It controls the extruder 303, which comprises a syringe and plunger in one embodiment. The movement of the linear motion stage 301 determines the flow rate of the wax printing. It also hosts a stepper motor connected to the plunger for the mixing function. An adaptor board can be used to provide a mounting location for the parts and determines the spatial positions between the 5-axis stage 304 and linear motion stage 301.

Figure 3:
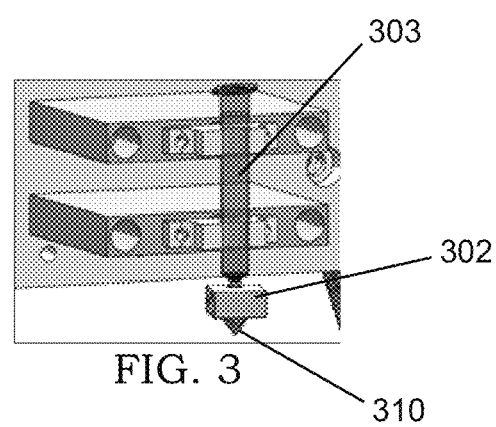
FIG. 3 is a component of the printer shown in FIG. 2.

To achieve favorable viscosity of the polyester wax, the to-be-printed wax is heated to near its melting temperature. The heating system 302 may comprise a heated nozzle (see FIG. 3) and/or a heated chamber. The nozzle heating system is comprised of a heating block, a cartridge heater, and a thermistor. In one example embodiment, the chamber heating system is comprised of two ceramic heaters; the nozzle heater comprises a commercial heating block (HICTOP®), which possesses a M6 threaded hole to connect nozzles (Micro-Swiss®), a through hole to hold the cartridge heater (Ivelink®), and a small hole to hold the thermistor. The chamber system heats the wax in the extruder before and during printing and keeps the viscous state of the printed wax on the substrate 308, which enables and facilitates the fusion between layers. A thermistor can be attached next to the syringe barrel of the extruder 303 to monitor the chamber temperature.

Figure 4A:
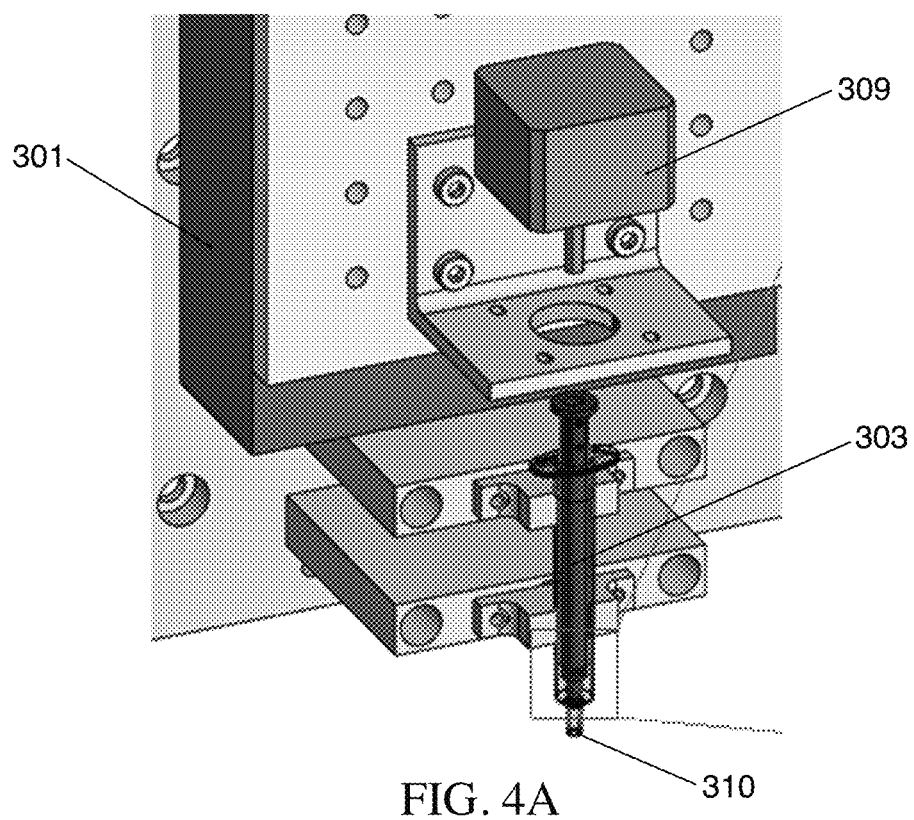
FIGS. 4A-4B show additional components of the printer.
Figure 4B:
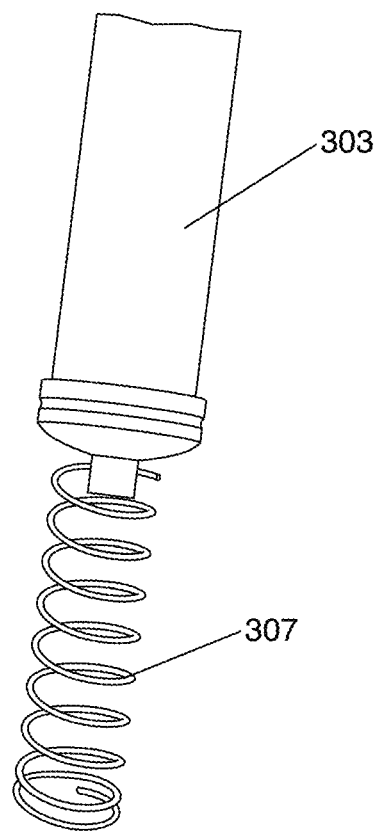

In a typical extruder, a syringe plunger moves downward to press material out of the nozzle. However, the wax used in the current method does not reach a homogenous texture with a favorable viscosity from mixing alone. As such, a extruder 303 incorporating a mixer 307 is used, as shown in FIGS. 4A-4B. As shown in FIG. 4A, the extruder 303 comprises a syringe that incorporates a compressible mixer 307. In one embodiment, the compressible mixer 307 comprises a spring and is connected to a first end of the plunger of the extruder 303. The opposing end of the plunger is connected to a stepper motor 309 that is mounted on the linear motion stage 301. Thus, when the linear motion stage 301 travels up and down, the stepper motor 309 and the plunger move with it. Rotation of the stepper motor 309 causes the plunger and the compressible mixer 307 to rotate as well. Because the mixer 307 is compressible, mixing can continue as the plunger is depressed.

Figure 5:
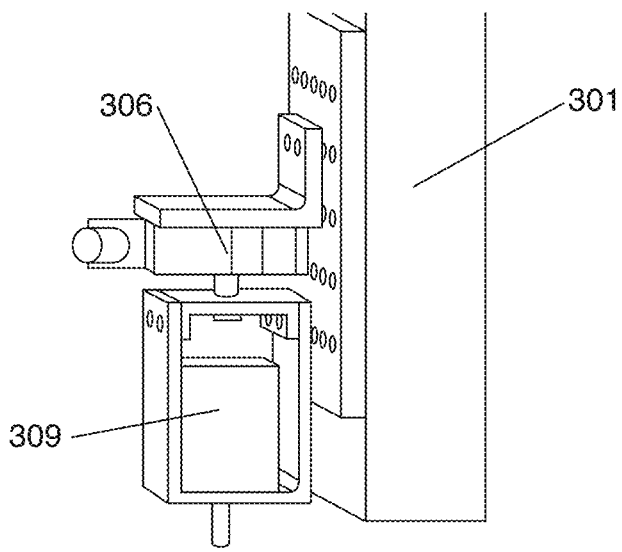
FIG. 5 shows a component of the printer according to an alternative embodiment.

In an alternative embodiment, a gauge 306 comprising a load cell is used to monitor the extrusion force without affecting the existing functions of the printer 300, as shown in FIG. 5. In this embodiment, the load cell is mounted between the linear stage 301 and the stepper motor 309. In some situations, it is beneficial to monitor extrusion force. For example, when smaller filaments are printed, the extrusion force increases exponentially as the diameter of the nozzle 310 decreases. Monitoring the extrusion force in real-time enables protection of the linear motion stage 301 from overload. Moreover, the extrusion force is related to the viscosity of the wax. Measuring extrusion force could provide details about the viscosity and homogeneity of the wax during printing.

A controller is used to coordinate the components of the printer 300. The controller maintains the temperature of the wax as its set-point using the nozzle heater and chamber heater, while the stepper motor 309 continuously mixes the wax in extruder 303 via the mixer 307. To initiate printing, a digital signal is sent linear motion stage 301 to start extruding. In some embodiments, a digital signal may also be sent to the stepper motor 309 to stop mixing. Next, the 5-axis stage 304 moves as prescribed and will determine the final geometry of the wax template 103. Finally, when the wax template 103 is completed, another digital signal is sent to linear motion stage 301 to stop extruding. If the mixing was stopped in a previous step, the stepper motor 309 is instructed to begin mixing again to maintain the consistency of the wax material within the extruder 303.

The diameters of the extruded filaments forming the template 103 can be controlled by varying the flow rate of the extruded wax and the transitional velocity of the 5-axis stage 304. The following equation shows the relationship between the process parameters:

$$D(Q,v) = \sqrt{(4Q/\pi v)}$$

where $D(Q,v)$ is the resultant filament diameter, Q is the flow rate of the extruded wax, and v is the transitional velocity of 5-axis stage 304. To keep the wax filament on the printing substrate 308 during printing, the distance between the end of the nozzle 310 and the substrate 308 is maintained around 0.8 D. Other distances may be used, however, the wax extrudates may stick to the nozzle 310 instead of staying on the printing substrate 308. To be able to remove the wax templates 103 easily from the substrate 308, a thin layer of a water-soluble material, such as Carboxymethyl cellulose (CMC) solution, can be coated on the printing substrate 308. After wax filaments are printed on the substrate 308, they can be separated from the substrate by liquefying and washing off the water-soluble coating using water. In an alternative embodiment, the surface quality of the template 103 can be improved by superficially heating the filaments to melt the exterior surface.

Figure 6:
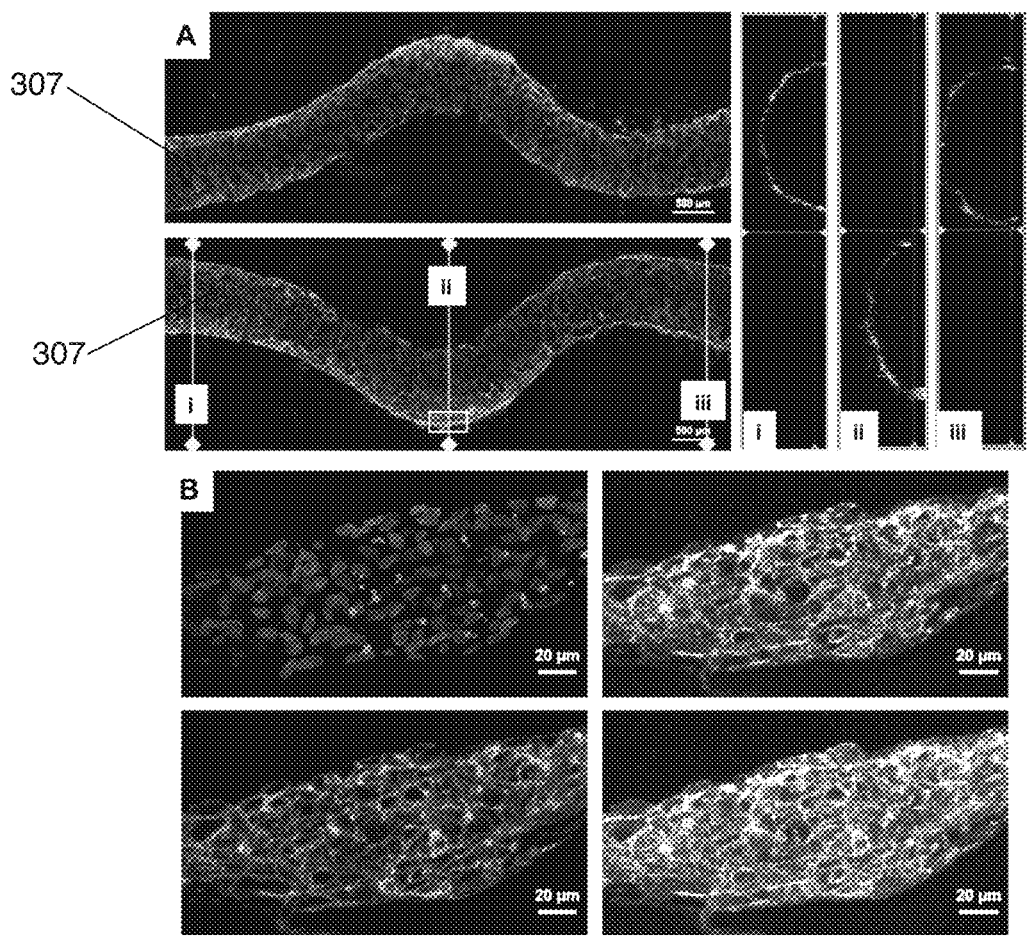
FIG. 6 depicts a vascular network created using the method of the present invention.

To evaluate the response of endothelial cells to the fabricated vascularized scaffolds 101, endothelial cell (HUVECs) were cultured in the vascular networks 102. Cell attachment to the circular lumen 106 walls was examined at days 1, 3, and 5 through immunofluorescence staining and confocal microscopy imaging. Representative images of the HUVECs culture as shown in FIG. 6. The lumen 106 is axially sliced into half before imaging due to the non-transparency of the hydrogel scaffolds 101.

In this example, the hydrogel scaffolds 101 were removed from a 70% ethanol solution and washed with sterile Dulbecco's phosphate-buffered saline (D-PBS or PBS) (ATCC® 30-2200™) for 24 hours with changing D-PBS twice. Fibronectin (cat #47743-728, VWR) at 100 ug/ml was added in the channels, rested in the culture hood for 3 hours, and then the scaffold 101 was flipped to coat the fibronectin on the other half of the channels.

Subsequently, the fibronectin-coated scaffolds 101 were pre-cultured in an incubator (Thermo Forma™ Series II 3110) at 37° C., 5% $CO_2$ for 2 hours in HUVEC growth medium (cat #CC5035, Lonza). After the hydrogel scaffolds 101 pre-cultured, $2.5 \times 10^6$ cells/ml HUVECs were pipetted to the lumens 106, and incubated for 1 hour to allow the cells in the medium to seed on the bottom half of the lumens 106. The lumens 106 were afterward washed by HUVEC medium to remove the unseeded cells. The same steps of HUVEC seeding were repeat three more times with the scaffolds 101 turned 90 degrees every time. The scaffolds 101 were in static culture overnight and followed by dynamic culture or continuous static culture for up to 7 days or 3 days.

The cell responses to the scaffolds 101 were assessed via immunofluorescence staining and confocal imaging at different days. The scaffolds 101 were fixed with 4% paraformaldehyde in PBS for 1 hour, permeabilized with 0.1% Triton X-100 for 30 minutes, and then treated with 1 wt % BSA for 30 minutes. The scaffolds 101 were washed using PBS in between each step. Subsequently, cells were incubated with: VE-Cadherin (cat #2500S, Cell Technology, 1:200) for 1 hours, followed by Alexa Fluor® 647 secondary antibody (cat #A21244, Life Technologies, 1:500) for 1 hour. A peristaltic pump with was used to perfuse the medium at a flow rate of 27.6 μl/min. As shown in FIG. 6, the HUVECs were consistently attached to the lumens 106.

While the disclosure has been described in detail and with reference to specific embodiments thereof, it will be apparent to one skilled in the art that various changes and modification can be made therein without departing from the spirit and scope of the embodiments. Thus, it is intended that the present disclosure cover the modifications and variations of this disclosure provided they come within the scope of the appended claims and their equivalents.

What is claimed is:

1. A method of fabricating a scaffold having a vascular network comprising:
   forming a template using a three-dimensional printer comprising an extruder incorporating a compressible mixer, wherein forming the template comprises:
   heating a thermally reversible material to a part-solid/part-liquid state,
   mixing the material in the part-solid/part-liquid state using the compressible mixer to obtain a homogenous texture,
   extruding the thermally reversible material in the part-solid/part-liquid state using the extruder while continuing mixing, and
   cooling the template to a solid state,
   wherein the template has a circular cross-sectional profile and has a shape of a vascular network;
   suspending the template in a reservoir;
   casting a hydrogel solution into the reservoir;
   lyophilizing the hydrogel solution to create a porous scaffold,
   wherein the template is embedded within the porous scaffold; and
   removing the template to create a scaffold having an embedded vascular network.

2. The method of claim 1, further comprising:
   crosslinking the scaffold.

3. The method of claim 1, wherein removing the template comprises:
   melting the thermally reversible material; and
   removing the thermally reversible material under vacuum pressure.

4. The method of claim 1, wherein the template forms a barrier between the porous scaffold.

5. The method of claim 1, wherein the thermally reversible material comprises a polyester wax.

* * * * *